United States Patent [19]

Horne

[11] 4,430,299

[45] Feb. 7, 1984

[54] APPARATUS FOR MONITORING CHEMICAL REACTIONS

[75] Inventor: Thomas Horne, Harpenden, England

[73] Assignee: Coulter Electronics, Inc., Hialeah, Fla.

[21] Appl. No.: 275,104

[22] Filed: Jun. 18, 1981

[51] Int. Cl.³ ............................................ G01N 35/04
[52] U.S. Cl. ..................................... 422/64; 356/246; 422/65; 422/66; 422/67; 422/102; 436/47; 436/48
[58] Field of Search ....................... 422/64, 67, 63, 65, 422/66; 356/435, 246; 364/497, 498

[56] References Cited

U.S. PATENT DOCUMENTS

| | | | |
|---|---|---|---|
| 2,554,414 | 5/1951 | McClendon | 422/91 |
| 3,918,910 | 11/1975 | Soya et al. | 422/66 |
| 4,160,646 | 7/1979 | Furatari et al. | 23/230 R |
| 4,224,032 | 9/1980 | Glover et al. | 422/64 |
| 4,234,540 | 11/1980 | Ginsberg et al. | 422/64 |
| 4,240,751 | 12/1980 | Linnecke et al. | 422/102 |
| 4,259,290 | 3/1981 | Suovaniemi et al. | 422/65 |
| 4,299,796 | 11/1981 | Esch | 422/65 |
| 4,308,231 | 12/1981 | Kolber et al. | 422/67 |

Primary Examiner—Michael S. Marcus
Attorney, Agent, or Firm—Silverman, Cass & Singer

[57] ABSTRACT

Apparatus for monitoring chemical reactions occurring on a slide, cartridge or other reflective carrier in which the nature of the reaction is determined quantitatively by means of a change in color. The reaction products are illuminated by radiant energy of a known wavelength and the reaction is detected and/or monitored by the reflection of the radiant energy from the sample where the reaction is occurring. A plurality of samples carried on such slides is disposed in alignment in a circle or a line and a rotor or carriage carrying plural photometers or a single photometer producing plural beams at different wavelengths is moved relative to the samples, the beams being directed at the samples. Each sample is scanned at least once as the carriage moves or the rotor rotates and the reflected radiant energy is captured by photo-responsive devices and channeled to a computer where the data is processed and information acquired concerning the respective samples with regard to end points and kinetic characteristics of their reactions.

24 Claims, 9 Drawing Figures

APPARATUS FOR MONITORING CHEMICAL REACTIONS

CROSS REFERENCE TO RELATED PATENTS

The application herein is to be considered with the disclosures of U.S. Pat. Nos. 4,234,538; 4,234,539; and 4,234,540 incorporated by reference. The assignee of this application is the owner of the above-identified patents. The applicant herein is one of the patentees of the said patents.

FIELD OF THE INVENTION

The field of the invention herein is the monitoring by means of radiant energy of the reaction or reactions of chemical specimens and more particularly is concerned with the monitoring of the absorption of radiant energy by specimens of blood, blood fractions or blood serum which have been treated with certain known reagents. The purpose of such treatment and monitoring is to ascertain the composition of the blood, blood fraction or serum quantitatively with respect to certain chemical constituents. The information which is derived enables the physician to diagnose illness, ascertain the physical condition of the patient whose blood serum is being tested and determine the efficacy of therapy.

BACKGROUND OF THE INVENTION

The nature of the invention and its background can be determined from the discussion in the patents which are incorporated herein by reference but a short explanation may be clarifying.

The so-called automatic chemistry apparatus which has become quite useful and advantageous in being able to assay many of the tests required in modern medicine is based upon the development of many different procedures for testing blood and blood serum. The technician generally dilutes the serum and adds one or two or perhaps even three reagents in certain quantities. The resulting sample is thoroughly mixed and incubated at a particular temperature or even cooled in certain cases. After a certain amount of time depending upon the nature of the test, the sample acquires a particular color. The technician directs the beam from a photometer that produces radiation of a particular wavelength and measures the amount of the radiation which is absorbed by the sample as a measure of a chemical constituent of the serum.

There are such tests for cholesterol, glucose, protein, calcium, albumin, uric acid and many enzymes.

The advantage of the automatic chemistry apparatus is that a large number of these tests can be conducted in a short time and in the case of a large hospital or testing laboratory the volume of testing required demands some form of automation.

Two aspects of such tests provide information to the physician and the researcher. The first is the end point of the test and the second is the kinetic progress of the test. Automatic chemistry apparatus have been developed and are in use at this time to provide end points, but there have been very few devices which enable the determination of the kinetic progress of a reaction.

The patents whose disclosures are incorporated herein teach an automatic chemistry apparatus which enables kinetic measurement of many samples by multiple wavelength radiation in a highly automated and reliable manner.

The device of said patents includes a turntable with sample support members such as cuvettes that are automatically provided with aliquots of samples, the turntable rotating slowly in a stepping action. After somewhat less than a revolution, the samples are removed, the cuvettes washed and tested in this condition and other samples introduced, the procedure being a continuous one. In the meantime a rotor carrying a plurality of photometers, eight in the incorporated patents, is rotating at a speed greater than that of the turntable, continuously scanning the sample support members but obtaining readings during dwell periods of the stepping movement. Each sample support member is therefore traversed by all of the beams of radiation many times before it has made the complete circuit of one revolution and a considerable amount of data has been obtained. This data is fed into a computer which computes the desired results and a readout is obtainable from the memory of the computer. The kinetic characteristic of each sample is available in addition to end points, either as a single value representing rate or as a series of values or in a graphic display.

In the above described apparatus, it is preferred that the sample support members comprise cuvettes which are transparent and that the beams of radiation pass into the cuvettes, through the aliquot or wash water or a blank which may be in the cuvette, out of the cuvette and thence to a photocell which responds to the amount of radiation which is not absorbed by the aliquot or sample. In such cases, it is obvious that the sample must be liquid, although the patents are not necessarily limited to transparent or translucent samples in transparent cuvettes.

In U.S. Pat. No. 4,234,539 there is disclosed and claimed a type of automatic chemistry apparatus in which, instead of a rotating turntable of sample support members carrying samples, the sample support members are contained in a carrier which is fixed and does not rotate. Such a carrier could be a disposable article or could be reused. It is intended to be mounted on the apparatus manually and removed when the tests are all completed or the carrier may be fixed and the sample support members individually removed or replaced selectively. The same rotor arrangement with multiple photometers is used, rotating at a relatively rapid rate to gain data concerning the aliquots carried in the sample support members or cuvettes of the fixed carrier. In the said U.S. Pat. No. 4,234,539 the rotation rate is about ten revolutions per minute.

This invention utilizes a circular, arcuate or rectilinear array of samples which is fixed and also a rotor or moving carriage which has a plurality of photometers whose beams scan the samples multiple times for the testing procedure, but the apparatus of the invention differs in the manner in which the samples are carried, the data is gathered and in many other respects.

Specifically, the samples of the invention herein are not arranged for transmission of radiant energy fully through the sample which is preferred by the inventions of the incorporated patents. The samples are disposed in a manner such that the reaction which occurs therein is measured by reflectance. This will be described in detail hereinafter.

Recently a type of apparatus has been developed by the several different groups including Kodak Ektachem Clinical Chemistry Products division of Eastman Kodak Company which utilizes what are termed "slides" which may be about the same size as laboratory glass slides. The slides are in the nature of cartridges because they are used once and then discarded. These slides are sample-carrying members which have the necessary reagents for chemical tests already in place. The user applies a drop or so of serum, plasma or whole blood to the slide at a particular location and then measures the reaction by reflecting light from the location where the reaction is occurring, thereafter picking up the reflected light in a photocell.

The details of one embodiment of this technique are published in the following references:

"Clinical Chemistry System With No Wet Reagents", Clinical Lab Products, Volume 7, Number 10, October 1978;

"Evaluation of an Engineering Model of the "EK-TACHEM" Analyzer for Glucose and Urea Assay" Cate, et al, Clinical Chemistry, February 1980, p. 266 to 270;

"A New Technology for the Clinical Laboratory" Przybylowicz, paper presented at American Association for Clinical Chemistry Meeting, San Francisco, California, July 23-28, 1978.

There are some important disadvantages of the apparatus which is disclosed in the above references and these relate to the amount of information which can be obtained, the throughput of samples and the complexity of the apparatus. For example, there is only one measuring position for all photometric tests as a result of which there is a very low throughput for rate reactions.

There is also a distinct disadvantage of the apparatus of the incorporated patents which utilizes a rotating turntable of cuvettes. The time for a complete revolution of the turntable is of the order of ten minutes and this means that an aliquot will remain on the turntable all that time. If the end point of the reaction has been reached some time before ten minutes have elapsed, the remaining time is wasted because the particular aliquot has to work its way around to the wash station even though the computer has already recorded the end point and may have noted that the reaction characteristic is now linear.

If liquid samples are being used with the fixed carrier of U.S. Pat. No. 4,234,539 the carrier cannot be removed from the apparatus until all tests are completed in which case any that have gone to an early end point must remain until the end of testing.

The invention herein obviates the disadantages mentioned bove.

SUMMARY OF THE INVENTION

Apparatus for monitoring chemical reactions in which the reactions occur on a slide or cartridge which is principally reflective and in which the reaction which occurs is measured quantitatively by detecting, in a photoresponsive device, the change of color of a sample carried on or in the slide, there being a beam of radiation directed at the sample and to a significant extent reflected therefrom onto the photoresponsive device.

The apparatus comprises two principal types of device, rotary and non-rotary.

In the rotary device a fixed support is provided with a circular array of cartridge-holding receptacles, each having provision for retaining a sample slide or cartridge in measurement position while being identified by suitable means and maintained at a constant temperature. A central rotor arranged coaxial with the array carries a plurality of photometers, each providing a radial beam of radiant energy directed to impinge sequentially against the cartridges, the cartridges being tilted to receive the beams and reflect a significant portion of the beams to the photoresponsive devices associated respectively with the photometers. Each photometer may be at a different wavelength although for certain purposes one or more may be at the same wavelength.

The cartridges are inserted through suitable slots in the cover of the apparatus into position in their respective receptacles and the rotor is rotated to derive the data of the reactions. Any cartridge may be inserted or removed at will without disturbing any of the other cartridges and without stopping rotation of the rotor. An identifying visible signal may inform the operator when the reaction of a particular cartridge has been measured.

In the non-rotary device a fixed support is provided with a linear array of cartridge-holding receptacles, each receptacle having provision for retaining a sample slide or cartridge in measurement position while being identified by suitable means and maintained at a constant temperature. The array can be rectilinear or arcuate instead of forming a closed circle. Instead of a rotor with plural radial photometers, there is a carriage which slides or rolls along a confining track or guideway parallel with the line of disposition of the array, the carriage mounting a single photometer whose primary beam is directed to intersect the line of the sample slides when mounted, normal thereto. A rotary filter wheel, grating or prism is interposed in the photometer beam. For the purpose of producing plural sub-beams of different wave-lengths the carriage mounts the beam dividing means and photo-responsive means to receive the sub-beams. The carriage is driven to step from cartridge to cartridge in a program of movement which will carry it back and forth along its guideway so that it can make measurements of each slide or cartridge a plurality of times.

As in the case of the rotary device, the cartridges are inserted through suitable slots in the cover of the apparatus into position in their respective receptacles and the carriage is stepped along its guideway to derive the data of the reactions. Any cartridge may be inserted or removed at will without disturbing any of the other cartridges and without stopping the travel of the carriage along its guideway. The same type of identifying signal may inform the operator when the reaction of a particular cartridge has been measured, thus enabling that cartridge to be replaced while the reactions on other cartridges continue.

The signals derived from measurements are converted from analog to digital data preferably on the rotor or carriage and multi-plexed to be transmitted to a computer.

DESCRIPTION OF THE PREFERRED EMBODIMENTS

The apparatus of the invention is basically comprised of a support or fixed part and a driven or moving part. The samples which are to be tested are carried on the fixed part in a novel arrangement which disposes them on an angle facing downwardly and the moving part carries the photometer means which direct beams at the samples, the radiant energy being reflected to photoresponsive devices arranged vertically which gather the information from the samples. The invention provides identification of the samples and indication for the operator of the earliest time that each sample can be removed and replaced by another.

Figure 6:
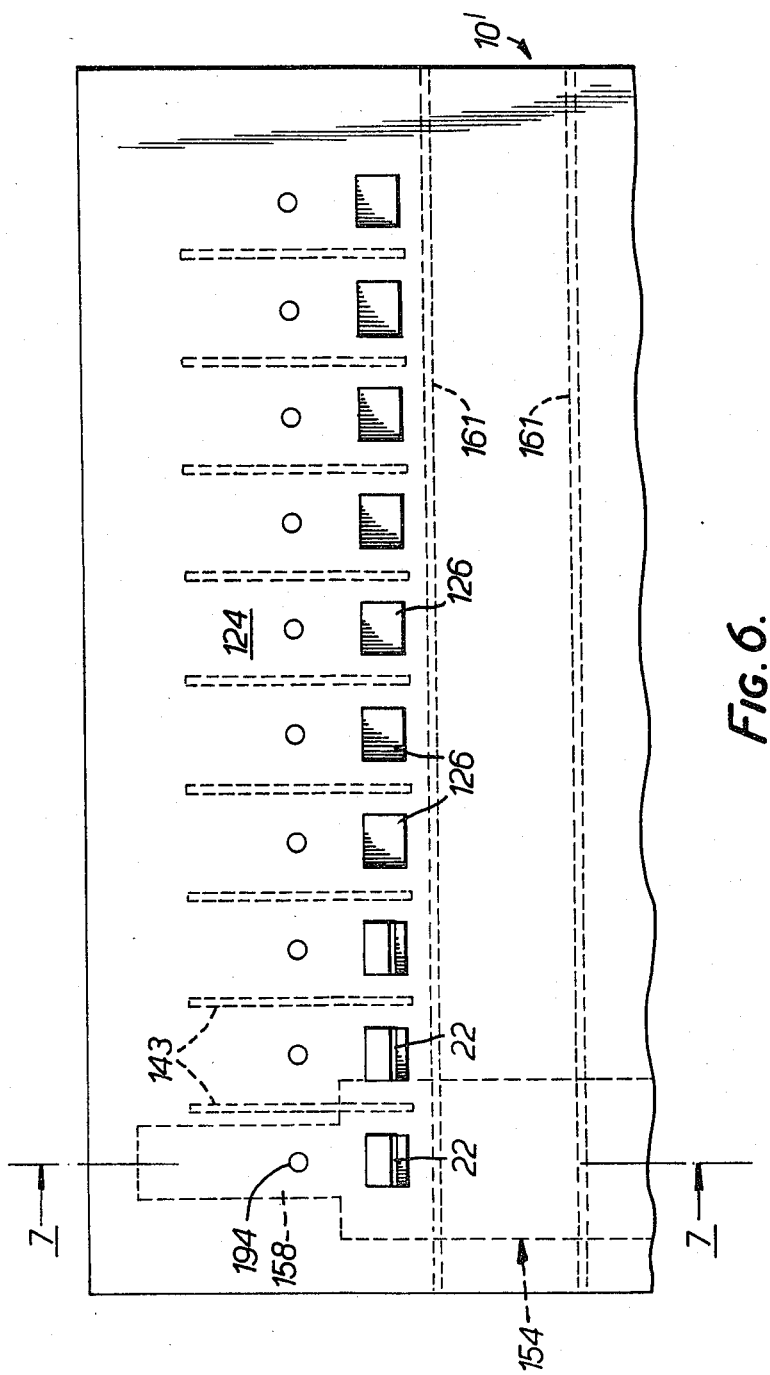
FIG. 6 is a fragmentary top plan view of an apparatus comprising a modified form of the invention wherein the photometer carrying means are non-rotary.
Figure 7:
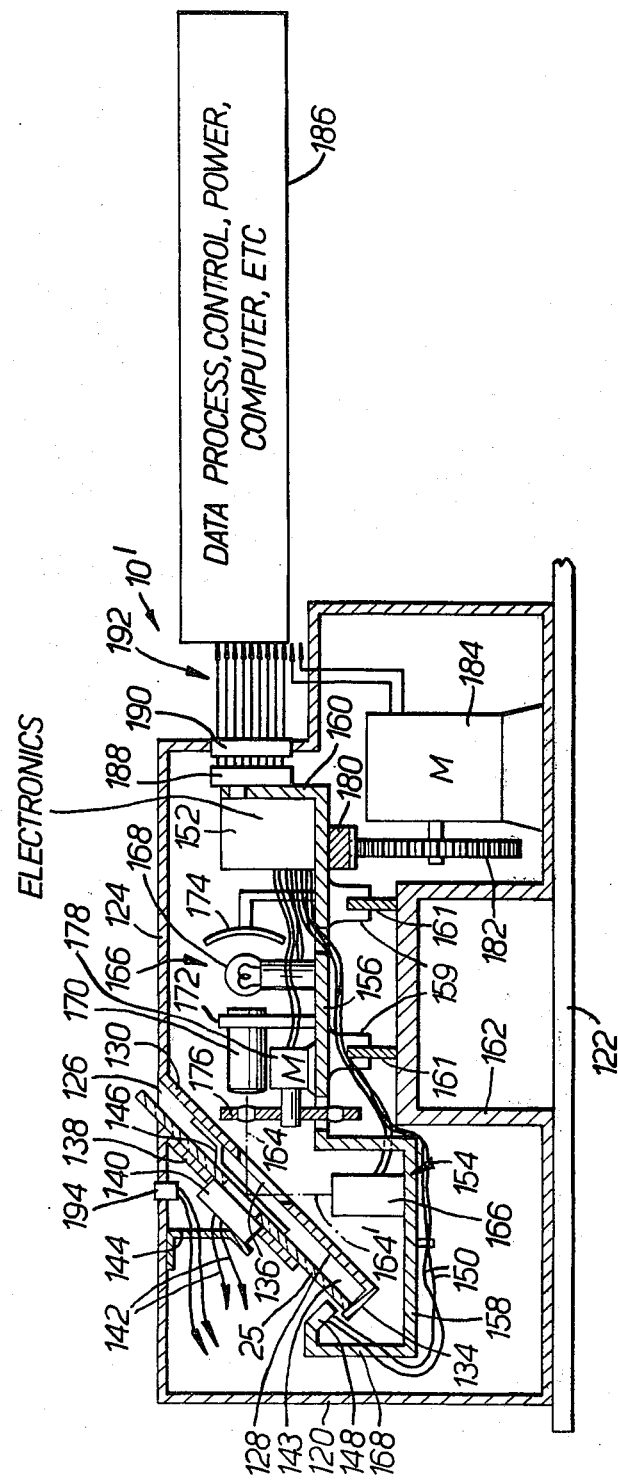
FIG. 7 is a fragmentary sectional view through the apparatus of FIG. 6 taken generally along the line 7—7 and in the indicated direction, portions being shown in elevation, the view being diagrammatic in certain respects.

Coming now to the details of the invention, the first apparatus to be described will be one in which the photometer means are mounted on a rotor. This embodiment of the apparatus of the invention is designated 10 and is illustrated in plan in FIG. 1 and in section in FIG. 2. There is a support or housing 12 which carries an upper casing 14 that mounts a top cover 16. A flanged joint is shown at 18 but the sheet metal details of the apparatus are not of significance, any suitable technique for forming the exterior and supporting parts of the apparatus being usable. The only structure of the exterior of the apparatus 10 which is of importance is the top cover 16 which will be detailed below. It should be borne in mind that the views of the apparatus 10 and the designated 10' in FIGS. 6 and 7 are principally diagrammatic.

The top cover 16 has a circular array of slots 20 into which the cartridges which carry samples are to be inserted. Such a cartridge of typical construction is shown in perspective at 22 in FIGS. 3 and 4 and it is formed as a slide or the like based upon a film or glass substrate 23 that is preferably transparent. Each cartridge 22 has a central sample receiving location 24 where the sample of blood serum will be applied. The body 25 of the slide is preferably of some liquid impervious material such as waterproof paper or synthetic resin that is nonreactive with the chemicals being used.

The slide or cartridge 22 is often referred to herein in a generic sense as a sample support member because in the apparatus of the invention it serves the same purpose as a cuvette in the patents that are incorporated herein by reference. The principal difference is that where a cuvette is used and is required to carry a liquid sample, the measurements are intended to be transmittance of radiant energy through the sample and/or scattering of radiant energy by the sample. In this invention the sample which is supported by the sample support member is dry and the measurements made are reflectance and to extent scatter. Transmittance measurements are not provided for; hence the sample support member and the sample overall may be opaque. As seen, there is a requirement in the cartridge 22 that the radiant energy beam pass through the substrate into the interior of the cartridge, but it passes out of the cartridge by reflectance through the same substrate.

As will be seen, some forms of cartridge do not utilize a transparent substrate and are not required to transmit any radiant energy through such substrate.

The central sample receiving location 24 of the cartridge 22 is in the upper surface of a sort of capsule of plural layers or lamina confined in a rectangular well 26 that extends fully through the cartridge body 25 but not through the substrate 23. The bottom of the well 26 is therefore closed off by a transparent window 27. The capsule which is carried in the well 26 in the illustrated example is formed of the top layer 28 and the central layer 29. The top layer is porous but inert and is preferably white. It may contain some type of clay or similar dispersed material such as titanium dioxide and its purpose is to spread the minute quantity of liquid sample that is applied to its exterior and transport it evenly to the central layer 29.

The central layer 29 is a porous layer also but it contains one or more chemical reagents in dry form that will react when moistened to produce some typical quantitative reaction identified by a particular color or changing color. There may be several such layers for some reactions. The color is "seen" through the window 27 by a beam of radiant energy such as 94 and emerges through the window most significantly as a reflected beam at 94', modified optically by the color of the reaction. Minor reflections and scattered light represented by the several short broken lines of FIG. 4 also emerge but may not be significant.

The chemicals in layer 29 are measured so that the application of a specific amount of serum or plasma or even whole blood will produce the quantitative reaction and desired change of color in the layer 29. The serum is adsorbed by the spreading layer 28 which as stated can be some kind of absorbent material and moves by capillary action evenly to the layer 29 to react with the reagent or reagents carried in that layer to produce the desired reaction.

As stated above the substrate window 27 of cartridge 22 is transparent or translucent so as to enable a sufficient amount of radiant energy to reach, be reflected by and leave the layer 29 when the reaction is occurring and/or has occurred.

The cartridge 22 may have a bar or other machine-readable code applied at its end 30 which is an identification of the patient from whom the serum sample was taken and could include test instructions. This could be for example on a self-adhering small slip of paper that the technician applies to the vial at bedside, easily removed and transferred to the cartridge when the tests are being conducted. Any other form of identification could be applied at this end 30. Permanent identification of the tests represented by reagents in areas 26 and 28 is preferably applied also at or near the area 30.

The slots 20 lead to respective sample chambers 31 within the apparatus 10, the chambers 31 being formed by the conical mask 32 that is connected to cover 16 in the illustration and which has a foot or ledge 34 that provides stop means for the insertion of the cartridges 22. The angle of the mask 32 is 45° in order to dispose the cartridges at that angle. There are sixty slots 20 in the cover 16 as shown and likewise there are sixty slits 36 in the mask 32 each slit 36 being aligned with the sample chamber 31 which is to receive a cartridge 22. When the cartridge is fully within its chamber 31 with its lower edge engaging the ledge 34 the slit 36 will be aligned with the sample area 24.

Each sample chamber 20 is also formed by a small flange 38 which can be connected with the upper cover 16 and could either be individual to each sample chamber 31 or in the form of a frusto-conical depending ring around the line of slots 20. Each flange or group of flanges 38 has a heater block 40 which is either engaged through a suitable opening in the flange 38 or is firmly engaged against the rear surface thereof to be in incubating position relative to a cartridge that may be engaged against the inside surface of the flange 38. The heater block 40 may be held in position by a small bracket 44 attached to the lower surface of the top cover 16. Wires 42 extend from the heater block 40 to a control center outside of the apparatus 10 where the incubating temperature of the block will be chosen.

Figure 5:
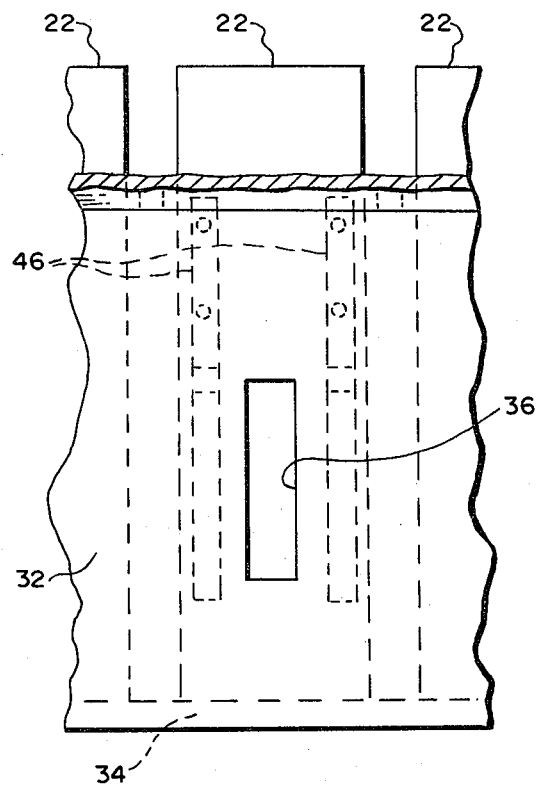
FIG. 5 is a fragmentary detailed view of a portion of the apparatus taken generally along the line 5—5 of FIG. 2 and looking at the rear of the support forming the receptacle for a slide or cartridge.

A pair of leaf springs 46 is secured to the mask 32 straddling the slit 36 (see FIG. 5) and arranged to press the cartridge 22 inserted into the chamber 31 tightly against the flange 38. This also positions the cartridge 22 accurately for the purposes of measurement. There are partitions between chambers 31 laterally thereof to prevent light scattering or other light interference between them.

Figure 3:
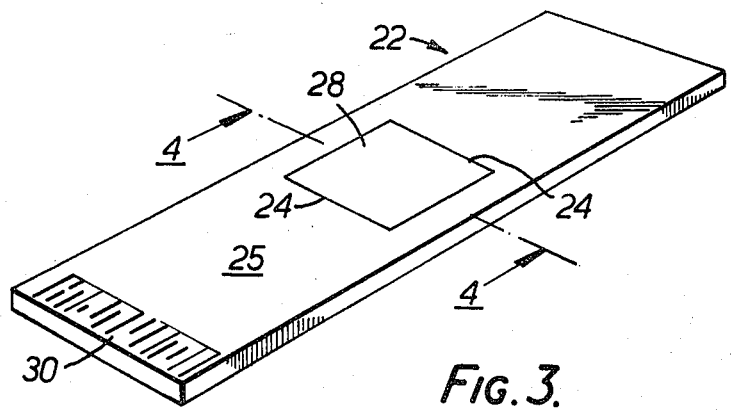
FIG. 3 is a perspective view of a slide or cartridge of the type which is used with the invention to carry the samples.
Figure 4:
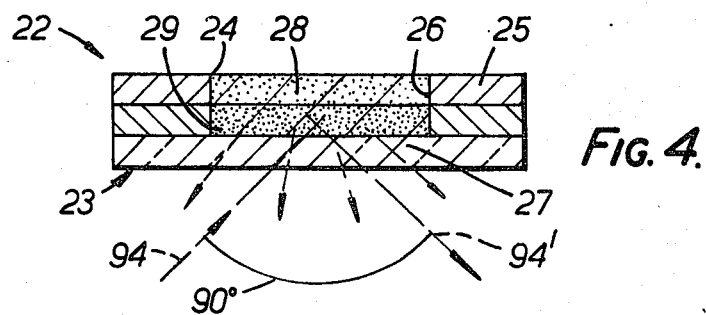
FIG. 4 is a transverse sectional view on an enlarged scale taken through the cartridge of FIG. 3 along the line 3—3 and in the indicated direction.

The bar code 30 can be on any convenient surface of the cartridge 22. In FIG. 3 it is on the surface to which the layer 28 is exposed, i.e., on the same surface as the sample receiving location 24. When a cartridge is in seated position in its chamber 31, the bar code faces upward at a 45° angle. One or more of the photometers has a reader device 48 which can be of any suitable electronic configuration to read the bar code 30 (or other machine-readable code) and transmit the information derived therefrom by means of the leads 50 which extend to the electronic circuitry 52 carried by the rotor 54.

There is a partition 56 carried on the support 12 which mounts a motor 58 whose shaft has a first gear 60 that drives the second gear 62 mounted on the rotor 54. The rotor 54 has a central passageway 64 in its hollow shaft 66 that is for carrying electrical leads and cables for different purposes. The lower extension 68 of the hollow shaft 66 is journalled on the partition 56 by means of a suitable bearing 70. The bottom end of the extension 68 engages the rotary part 72 of a slip-ring connector 74 whose fixed part 76 is mounted to the support 12.

Figure 1:
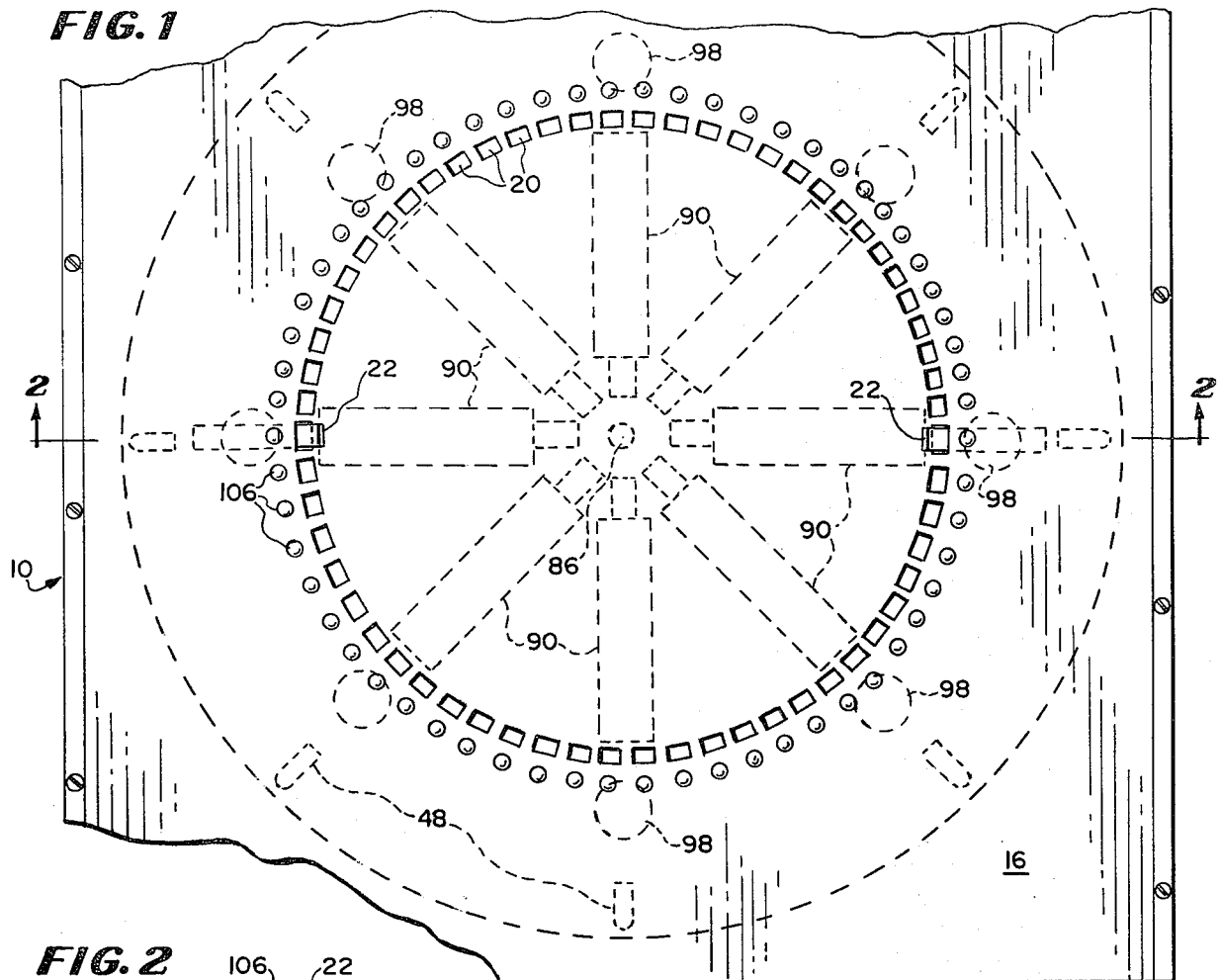
FIG. 1 is a fragmentary top plan view of an apparatus for monitoring chemical reactions constructed in accordance with the invention wherein the photometer carrying means are rotary.
Figure 2:
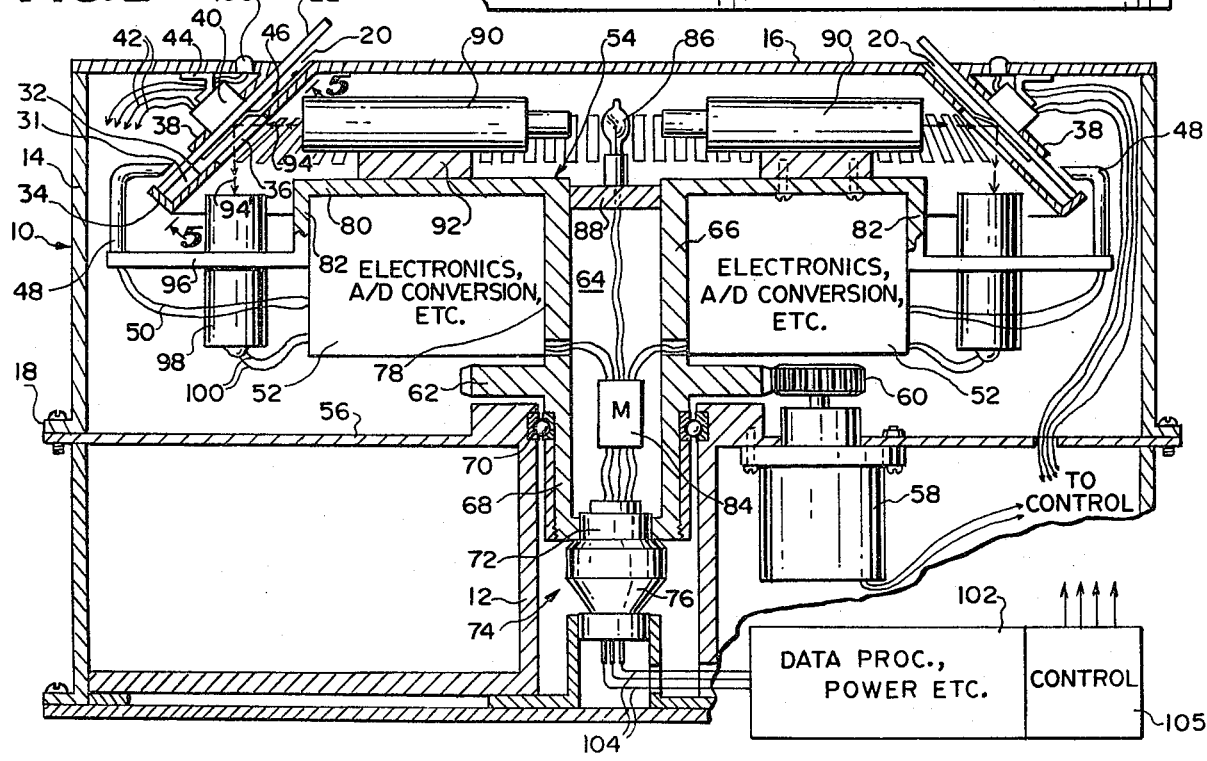
FIG. 2 is a medium sectional view taken generally along the line 2—2 of FIG. 1 and in the indicated direction, portions being shown in elevation, the view being diagrammatic in certain respects.

The rotor 54 has an annular chamber 78 formed by the top wall 80, the hollow shaft 66 and an outer annular wall 82 which provides space for the electronic circuitry 52 that is carried by and rotates with the rotor. This circuitry 52 may be in the form of printed circuit boards carrying electronic and electrical components to process analog signals to digital, co-ordinate the relationships between the signals and the identifying data picked up by the reader devices 48 etc. The circuitry 52 has output leads and control leads extended to the rotating part 72 of the slip ring device 74 which has electrical contacts at its upper axial end to which said leads are connected. In the case of the apparatus 10 which is illustrated in FIGS. 1 and 2 there are eight photometers and one or more identification reader devices. The number of connections which would be required for all of the electrical functions to be transmitted through the slip ring device 74 may be prohibitive for any practical device; hence there will be multiplexing of the signal transmission and multiplexing means will be provided with the circuitry 52. Symbolically a block marked "M" is shown at 84 within the hollow passageway 64.

There are eight photometers mounted on the rotor 54. Each photometer has a source of radiant energy such as a central lamp 86 which is carried on a support 88, the single lamp rotating with the rotor 54 and serving all of the photometers. There is an optical train for each photometer, symbolized by the tube 90 mounted on a pedestal 92 carried on the wall 80. The beam from the optical train 90 is shown at 94, entering the slit 36 of the mask 32 passing through window 27 and impinging against the reactive layer 29 of the cartridge 22 disposed on the opposite side of the mask 32. It is again noted that the reactive portion of the capsule can comprise several layers or lamina like 29.

The beam 94 extends horizontally as shown in FIG. 2 but inasmuch as the cartridge 22 is disposed at an angle of 45° the reflected beam 94′ will be directed downward. A platform 96 which is carried by the wall 82 mounts a photoresponsive device 98 such as a photocell or photodiode which may comprise a photomultiplier with its sensitive receptor element facing upward. The electrical leads 100 from the device 98 connect to the electronic circuitry 52. The reader device 48 is also mounted on this platform 96 to rotate with the rotor 54.

The arrangement which has been described is compact and simple in construction and provides an apparatus 10 that is simple and effective to use.

The operator chooses a cartridge 22 to perform the test which is desired. This cartridge may provide information for more than a single test because there will be eight photometers of different wavelengths illuminating the test area of the cartridge. (Suitable filters may be built into the optical train 90 of each photometer) He applies a small quantity of serum or other type of sample to the sample receiving location 24 and inserts the cartridge into an empty slot 20. He moves the cartridge into the chamber 31 as far as it will go. He may have already instructed the computer and control center what to do. The bar code area 30 in addition to giving information about the patient whose serum is being tested will normally also give information to the computer as to what tests are being performed.

The cartridges can be installed or removed without stopping the rotation of the rotor 54. The data output from the apparatus 10 is continuously being passed to the data processing equipment 102 through the leads 104 that connect to the fixed portion 76 of the slip ring device 74. Power for the circuitry 52 and the source of radiant energy 86 is transmitted to the rotor 54 in the same manner from exterior of the apparatus 10.

The data processing equipment 102 will normally include a computer which will have a memory that can be programmed to perform much of the control of the apparatus. The control section is shown at 105.

The apparatus 10 is capable of providing a signal which will instruct the operator when to remove and replace a cartridge. Each of the slots 20 is shown provided with an adjacent signal light 106 which could be a lamp or a light emitting diode operated under the control of the computer. The computer can be instructed that when a particular test is to be carried out, the test will be completed in a set time or when a particular reaction condition has been achieved. At this point a signal can be produced which turns on the lamp 106 alongside the slot in which the cartridge is disposed signalling the operator to remove the cartridge and insert another. Removal of the cartridge could trigger resetting of the system in readiness for insertion of the next slide or cartridge.

The heaters 40 can also be controlled by the computer to provide the exact temperature needed for any particular test or group of tests. Thus, the bar code can also provide the information needed for the computer to signal the control center 105 to energize the particular heater 40 to some specific temperature and maintain that during the test or tests.

Assuming that the rotor 54 rotates at ten revolutions per minute, there will be 80 readings taken of each sample every minute since there are eight photometers. The total number of readings taken per minute would be 4800 and the total number of readings per hour would be 288,000. If we assume that it requires one minute to load and read end points, results would not commence to be obtained for a minute and thus there could only be sixty end points obtained every minute, one for each sample irrespective of the number of readings taken. This would provide 3600 results per hour.

As for rate reactions, if we assume that it requires a full five minutes for a complete rate reaction to be obtained, then the number of kinetic characteristics which could be obtained in an hour is 720. Kinetic reaction measurement and data require multiple readings at relatively short intervals high speeds and the apparatus is especially adapted for such use.

FIGS. 6 and 7 illustrate a second embodiment of the invention which aligns the cartridges 22 in a rectilinear disposition. The apparatus 10' which is shown utilizes a lesser number of cartridges, can be made smaller and less complex than the apparatus 10 and hence will be less expensive to manufacture. The principles of operation and the general construction are quite similar to the apparatus 10.

Although not illustrated, the disposition of the cartridges 22 can be in an arc of a circle instead of a complete circle as in apparatus 10 requiring some structural modification over that which will be described for the apparatus 10'.

The apparatus 10' comprises a frame or housing 120 mounted on a base 122 and having a cover member 124 having an array of slots 126 into which the cartridges 22 are to be inserted. The construction of the cartridges and the manner in which they are used are identical to that already described. The slots 126 lead to respective sample chambers 128 within the apparatus 10', the chambers being formed by a depending mask 130 that is connected with the cover member 124 and may be in the form of an elongate flange extending the length of the cover member 128. There is a right-angle bent foot or ledge 134 that provides stop means for the insertion of the cartridges 22. The angle of the mask is 45° in order to dispose the cartridges at that angle.

In the apparatus 10' there are ten slots 126 in the cover member 124 and likewise there are ten slits or windows 136 in the mask 130, each slit 136 being aligned with the sample chamber 128 which is to receive a cartridge 22.

When the cartridge is fully within its chamber 128 with its lower edge engaging the ledge 134 the slit 136 will be aligned with the window 27 of the cartridge 22.

As in the case of the apparatus 10 each of the chambers 128 is also formed by a second flange 138 which is connected with the upper cover member 124 and could either be individual to each sample chamber 128 or in the form of an elongate depending flange extending along the line of the slots 126. A heater block such as shown at 140 may be provided for each chamber 128 mounted on or extending through the flange 138 forming each chamber or a group of chambers. There could be suitable openings in the flanges 138 to accommodate the heater blocks and thereby enable the heater blocks to serve as incubating means engaged against the cartridge or cartridges 22 or the flange 138 is an elongate unitary structure could have the heater block or blocks 140 snugly engaged against its rear surface in position to warm parts or all of the flange for incubating purposes.

The electrical wires for the power of the heater blocks 140 will extend externally of the apparatus 10' to the control or computer station. Such wires are shown at 142. The heater block or blocks 140 may be held in position by small brackets 144 which are attached to the lower surface of the cover member 124. Partitions 143 are installed between the chambers or receptacles 128 to isolate the chambers 128 from one another optically and thermally.

The bar code 30 on the surface 25 of the cartridge 22 opposite the surface formed by the substrate 23 faces upward at an angle of 45° when the cartridge 22 is in seated position within a chamber 128. At this time, a pair of leaf springs 146 in each chamber identical to springs 46 of apparatus 10 will hold the cartridge tightly against the flange 138. In this position, the bar code 30 can be read by a suitable reader device 148 which can be of any electronic configuration to read the bar code 30. Obviously other types of machine readable codes could be used in place of the bar code 30. The reader device 148 is carried by the photometer which shortly will be described and its electrical leads 150 are shown connected to electronics circuitry 152 mounted in a manner which will be described.

In the case of the apparatus 10 it will be recalled that there was a rotor 54 which mounted a plurality of photometers. In the apparatus 10' there is a single photometer which is mounted on a sliding carriage and which, by means of a rotary filter, grating or prism produces a plurality of light beams at different wavelengths from a single lamp.

Looking now at FIG. 7, there is a carriage 154 which has a central section 156, a left hand extension 158 and a right hand extension 160. On the bottom of the central section 156 there is a pair of sliders 159 which are engaged upon a pair of slides or a track 161 mounted on the platform 162 connected to the base 122. Any suitable arrangement can be used, as for example, rollers on guideways and the like, so long as the carriage 154 is capable of smooth and accurate movement along the line of the slots 126. The slides 161 confine and guide the movement of the carriage 154 along the length of the apparatus 10' so that the photometer beam 164 can be brought sequentially into alignment with the slit 136 of each chamber 128.

The photometer is designated generally 166 and comprises a lamp 168 mounted on the central section 156 of the carriage 154, an optical collimating structure 170 mounted on a suitable bracket 172 and a reflector 174 behind the lamp 168 to concentrate its light to the left as shown in the view. A filter wheel 176 is fixed to the shaft of a small motor 178 carried on the central section 156. Leads are shown connecting the motor 178 and the lamp 168 to the electronics circuitry 152 that is mounted on the extension 160.

The beam 164 is formed of multiple wavelengths as the filter wheel is turned and passes through the slit 136, engages into the capsule of the cartridge 22 and is reflected back out at 90° relative to the main beam 164 as shown at 164'. A photocell 166 or other photoresponsive device is mounted on the extension 158 along with the bracket 168 that carries the code reader 148. The leads connected to these devices extend to the electronics circuitry 152.

Instead of the filter wheel 176, there could be prisms or a grating in alignment with the beam 164' so that the reflected beam can be broken up into plural wavelengths. The photoresponsive device 166 in such case would be required to have a plurality of components aligned with the respective beams for responding to the different wavelengths.

On the bottom of the extension 160 there is provided a geared rack 180 engaged with a gear wheel 182 driven by a stepping motor 84 mounted on the base 122. The motor is connected by suitable leads to the control console 186 which provides the necessary commands and power to drive the motor 184 so that it is properly positioned and moved for the purposes of the apparatus.

The carriage 154, as will be noted, carries several different electrical components which require power, control, and which produce signals. These include the reader 148, the photoresponsive device 166 (which may be compound and have the connections for several channels of signals), the lamp 168 and the small motor 178. In addition to these components, the electrical circuitry 152 may include amplifiers, A/D converters, a multiplexer, etc. The power and control connections are required to be brought out to the computer, data processing equipment and control console or center 186. This is effected either by a slip contact device or by flexible cables. Shown in FIG. 7 is a slip contact device which has a part 188 that is carried by the carriage 154 and has a plurality of slider members facing slides carried by support 190 extending along the length of the housing 120 to follow the movement of the carriage and provide the necessary electrical contacts. Electrical leads or cables 192 extend to the console 186.

In operation, the device 10' utilizes an economy of parts compared with the apparatus 10. The carriage can be instructed to move in a program which will carry it along the length of the slots 126 in one direction, stepping from slot to slot and stopping at each one long enough to make the measurements of the sample carried by the cartridge 22 at each position. When the carriage reaches the end of the line of slots it can be programmed to return to the first one or it can be programmed to start back along the positions in reverse. The carriage likewise can be programmed to skip any slot where a cartridge has been removed, can be instructed to spend different time durations at different positions, etc.

The apparatus 10' may be provided with the same type of circuitry for signalling when a reaction has reached a certain point by means of the signal lamps 194 in the manner described for the lamps 106 of apparatus 10.

The apparatus 10' provides a smaller device which has great flexibility in use. It is ideal for small laboratories, hospitals and clinics and could be of value in doctors' offices or at the patients' bedsides.

Figure 8:
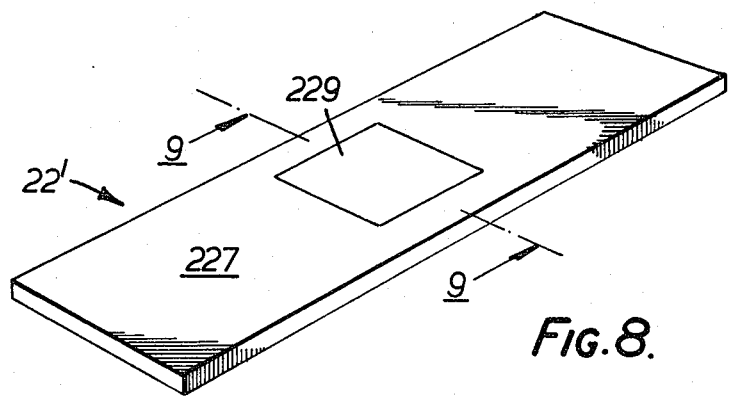
FIG. 8 is a form of slide or cartridge useful with the invention which has a construction differing from that of FIGS. 3 and 4.
Figure 9:
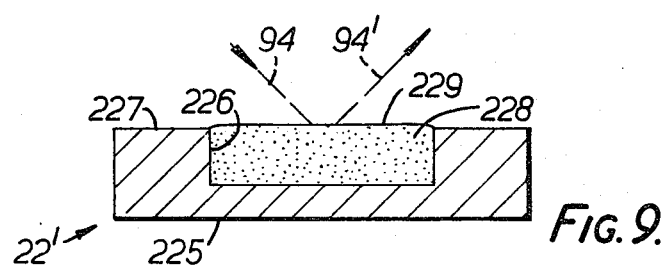
FIG. 9 is a sectional view taken through the cartridge of FIG. 8 along the line 9—9 and in the indicated direction.

In FIGS. 8 and 9 there is illustrated an alternate form of cartridge 22'. A rectangular body member 225 has a well 226 opening to the surface 227, the well being blind at its bottom end. A dry capsule 228 containing all of the reagents compacted into a unit is contained in the well 226. Its upper surface 229 is the sample applying area. A drop of serum is applied, will spread through the capsule 228 and provide the change of color to be reflected at 94' when exposed to the beam 94.

Many variations are capable of being made without departing from the spirit or scope of the invention as defined in the appended claims.

What it is desired to secure by Letters Patent of the United States is:

1. Apparatus for monitoring chemical reactions occurring or having occurred in a plurality of sample substances carried respectively by a plurality of cartridges of generally strip-like planar construction, the reaction occurring or having occurred in any cartridge being detected by directing a beam of radiant energy to illuminate a cartridge at a radiant energy receiving surface thereof which provides access to said substance carried by the cartridge and measuring the modified radiation reflected from the sample substance carried by said cartridge and the radiant energy receiving surface, said apparatus comprising:

A. a stationary support structure,

B. a plurality of cartridges of generally strip-like planar construction,

C. means on said structure for fixedly supporting a plurality of said cartridges in a geometric line array and each cartridge having a sample substance carried thereby and a radiant energy receiving surface providing access for radiant energy to said sample substance, the radiant energy receiving surfaces of all said cartridges facing to the same side of said array, said cartridges being supported by said supporting means in such a manner as to enable the removal and replacement of any one independently of all others, D. a movable carrier on said support structure and means mounting said movable carrier for guided movement substantially parallel to said geometric line, E. at least one photometer carried on said movable carrier, said photometer having a source of radiant energy and means forming a beam of said radiant energy and directing said beam to said cartridges, the formed beam being disposed to impinge against said cartridges at the radiant energy receiving surfaces thereof as the movable carrier moves relative to said array, F. the angle of impingement of said beam with said radiant energy receiving surfaces relative to the planes of said surfaces being such as to enable detection of reflected radiant energy, G. said photometer including photoresponsive means on the same side of said surface as said beam arranged to receive modified radiation reflected from said cartridges directly from said surfaces, the spatial relationship of the beam forming means and photoresponsive means being fixed, H. means for moving the movable carrier on a program of movement to direct said beam at the cartridges selectively if not sequentially, the cartridge support being such that said removal of any one of said cartridges from said support being accomplished without interruption of said program of movement of said movable carrier, I. the photoresponsive means being responsive to the modified reflected radiation to produce an electrical signal related to the chemical condition of the sample substance, if any, carried by the cartridge which the directed beam illuminates, movement of the movable carrier serving to produce a plurality of said signals from the sample substances of those cartridges which have been illuminated, J. means for generating usable data from said signals and K. means for coupling the signals from the carrier to said last-mentioned means.

2. The apparatus as claimed in claim 1 in which the movable carrier is a carriage, the geometric line is rectilinear and the mounting means comprise cooperating track and trackriding means on the carriage and support structure.

3. The apparatus as claimed in claim 1 in which there is a plurality of photometers mounted on the movable carrier and said photoresponsive means include plural devices for receiving radiation from the respective beam forming means of said photometers.

4. The apparatus as claimed in claim 1 in which the movable carrier has circuitry mounted thereon for converting analog signals produced by said photoresponsive means to digital signals and the coupling means transmit only signals from said photoresponsive means which are digital.

5. The apparatus as claimed in claim 1 in which the said coupling means comprise slide and slider means mounted on said movable carrier and said support structure.

6. The apparatus as claimed in claim 1 in which the means for moving the movable carrier comprise a stepping motor and the program of movement comprises stepping the movable carrier from cartridge to cartridge, dwelling at any cartridge and moving to another cartridge.

7. The apparatus as claimed in claim 1 in which means are provided for dissecting the beam directed to said cartridges into multiple wavelength components whereby to illuminate each of said cartridges with different wavelengths of energy, the photoresponsive means being arranged to respond to said different wavelengths of energy.

8. The apparatus as claimed in claim 10 in which said dissecting means comprise a filter wheel carrying different filters and means on said movable carrier for rotating the filter wheel and bringing the different filters sequentially into the path of the directed beam.

9. The apparatus as claimed in claim 1 in which the movable carrier is a rotor mounted on an axis and the geometric line is a circle coaxial with said rotor.

10. The apparatus as claimed in claim 9 in which the said coupling means comprise a slip ring device having a rotary part and a fixed part, the rotary part having electrical connections from the rotor connected thereto and being secured to the rotor, the fixed part being mounted to said support structure and having connections to the usable data generating means connected thereto.

11. The apparatus as claimed in claim 9 in which the means for supporting the cartridges are arranged to tilt all of the cartridges when in position on an approximately 45° angle with the horizontal, facing the energy receiving surface of each cartridge inwardly toward said axis and downwardly, the directed beam of radiant energy being horizontal, the photoresponsive means having its active element facing upward and arranged to receive the reflected energy from said cartridges as said energy passes downward.

12. The apparatus as claimed in claim 9 in which there is a plurality of photometers on the movable carrier, said photometers being radially disposed on said rotor with each photometer forming a separate beam of radiant energy, the cartridges adapted to be facing inwardly and tilted downwardly when disposed on said supporting means, there being at least a separate photoresponsive device for each photometer arranged with a sensitive element facing upward to receive the reflected radiation from said cartridges.

13. The apparatus as claimed in claim 9 in which the means for fixedly supporting said plurality of cartridges are arranged to hold said cartridges in said circle in a disposition with the surfaces of said cartridges carrying said sample substances all facing said beam and being tilted relative to said beam whereby the beam will engage said substances and subtend an acute and an obtuse angle therewith, the modified radiant energy being reflected to the obtuse angle side of each cartridge and substantially diverted from returning along said beam, said photoresponsive means being located to receive said reflected and modified radiant energy.

14. The apparatus as claimed in claim 1 in which the means for fixedly supporting said plurality of cartridges are arranged to hold said cartridges in a disposition with the sample substances carried thereby facing said beam and with the angle between said beam and each of the radiant energy receiving surfaces when engaged by said beam being other than 90° whereby the modified radiant energy reflected from said surfaces is substantially diverted from returning along said beam, said photoresponsive means being located to receive said reflected and modified radiant energy.

15. Apparatus for monitoring chemical reactions occurring or having occurred in a plurality of sample substances carried respectively by a plurality of cartridges of generally strip-like planar construction, the reaction occurring or having occurred in any cartridge being detected by directing a beam of radiant energy to illuminate a cartridge at a radiant energy receiving surface thereof which provides access to said substance carried by the cartridge and measuring the modified radiation reflected from the sample substance carried by said cartridge and the radiant energy receiving surface, said apparatus comprising:

A. a support structure including a housing having a cover member, said cover member having a plurality of slots defining a geometric line, B. a plurality of cartridges of generally strip-like planar construction, C. means on said structure for fixedly supporting a plurality of said cartridges in an array along said geometric line and each cartridge having a sample substance carried thereby and a radiant energy receiving surface providing access for radiant energy to said sample substance, the radiant energy receiving surfaces of all said cartridges facing to the same side of said array, the said cartridge supporting means comprising receptacles below the cover member, each slot comprising the entrance to a receptacle, D. a movable carrier on said support structure and means mounting said movable carrier for guided movement substantially parallel to said geometric line, E. at least one photometer carried on said movable carrier, said photometer having a source of radiant energy and means forming a beam of said radiant energy and directing said beam to said cartridges, the formed beam being disposed to impinge against said cartridges at the radiant energy receiving surfaces thereof as the movable carrier moves relative to said array, F. the angle of impingement of said beam with said radiant energy receiving surfaces relative to the planes of said surfaces being such as to enable detection of reflected radiant energy, G. said photometer including photoresponsive means on the same side of said surface as said beam arranged to receive modified radiation reflected from said cartridges directly from said surfaces, the spatial relationship of the beam forming means and photoresponsive means being fixed, H. means for moving the movable carrier on a program of movement to direct said beam at the cartridges selectively if not sequentially, I. the photoresponsive means being responsive to the modified reflected radiation to produce an electrical signal related to the chemical condition of the sample substance, if any, carried by the cartridge which the directed beam illuminates, movement of the movable carrier serving to produce a plurality of said signals from the sample substances of those cartridges which have been illuminated, J. means for generating usable data from said signals and K. means for coupling the signals from the carrier to said last-mentioned means.

16. The apparatus as claimed in claim 15 in which each receptacle has a mask blocking the cartridge which may be disposed in said receptacle from the said source of radiant energy but for a slit to admit the beam, any reflected radiation from the cartridge being capable of passing back through said slit but on an alignment different from that of the directed beam, the photoresponsive means being located to receive the reflected radiation exclusive of any radiation from the directed beam.

17. The apparatus as claimed in claim 15 in which an identifying signal device is disposed on said cover alongside and identifying each slot and in which means are provided to operate said identifying signal device when the electrical signal from the sample substance of a cartridge in said slot has a predetermined character.

18. The apparatus as claimed in claim 15 in which partition means are provided separating the receptacles at least optically from one another.

19. The apparatus as claimed in claim 15 in which an identifying signal producing device is provided individual to each receptacle and said identifying signal producing device includes means for operating the identifying signal producing device of any receptacle when the electrical signal from the sample substance of the cartridge in said last mentioned receptacle has a predetermined character.

20. The apparatus as claimed in claim 15 in which each receptacle has a stop member to limit and define the extent to which a cartridge can be introduced into said receptacle.

21. The apparatus as claimed in claim 20 in which each receptacle includes spring means for holding the cartridge frictionally engaged therein.

22. Apparatus for monitoring chemical reactions occurring or having occurred in a plurality of sample substances carried respectively by a plurality of cartridges of generally strip-like planar construction, the reaction occurring or having occurred in any cartridge detected by directing a beam of radiant energy to illuminate a cartridge at a radiant energy receiving surface thereof which provides access to said substance carried by the cartridge and measuring the modified radiation reflected from the sample substance carried by said cartridge and the radiant energy receiving surface, said apparatus comprising:

A. a support structure including an enclosed housing,

B. a plurality of cartridges of generally strip-like planar construction,

C. said structure having means within said housing for accommodating and fixedly mounting a plurality of said cartridges in said housing in a circular array and each cartridge having a sample substance carried thereby and a radiant energy receiving surface providing access for radiant energy to said sample substance from the interior of said housing, the radiant energy receiving surfaces of all said cartridges facing radially inward, the housing having passageway means therein enabling insertion of said cartridges from the exterior of said housing into respective ones of said accommodating and mounting means, said passageway means and the accommodating and mounting means being geometrically related substantially to restrict external radiant energy from entering the interior of said housing, D. a rotary carrier on said support structure and means mounting said carrier coaxially with said array, E. at least one photometer mounted on said carrier and having a source of radiant energy and means forming a beam of said radiant energy and directing said beam to said cartridges, said formed beam being disposed to impinge against said cartridges at the respective radiant energy receiving surfaces thereof as the carrier rotates relative to said array, F. the angle of impingement of said beam with said radiant energy receiving surfaces relative to the planes of said surfaces being such as to enable detection of reflected radiant energy, G. said photometer including photoresponive means on the same side of said surface as said beam arranged to receive modified radiation reflected from said cartridges directly from said surfaces, the spatial relationship of the beam forming means and photoresponsive means being fixed, H. means for rotating said carrier any desired numbers of revolutions to direct said beam at the cartridges in sequence around said array, I. the photoresponsive means being responsive to the modified reflected radiation to produce an electrical signal related to the chemical condition of the sample substance, if any, carried by the cartridge which the directed beam illuminates, rotation of said carrier serving to produce a plurality of said signals from the sample substances of those cartridges which have been illuminated, J. said cartridge mounting means, housing and passageway means being constructed and arranged in such a manner as to enable the removal of and replacement of any one or more cartridge independently of all others and without interrupting the rotation of the carrier, K. means for generating usable data from said signal and L. means for coupling the signals from the carrier to said last-mentioned means.

23. Apparatus for monitoring chemical reactions occurring or having occurred in a plurality of sample substances carried respectively by a plurality of cartridges of generally strip-like planar construction, the reaction occurring or having occurred in any cartridge being detected by directing a beam of radiant energy to illuminate a cartridge at a radiant energy receiving surface thereof which provides access to said substance carried by the cartridge and measuring the modified radiation reflected from the sample substance carried by said cartridge and the radiant energy receiving surface, said apparatus comprising:

A. a support structure,

B. a plurality of cartridges of generally strip-like planar construction,

C. means on said structure for fixedly supporting a plurality of said cartridges in a circular array and each cartridge having a sample substance carried thereby and a radiant energy receiving surface providing access for radiant energy to said sample substance, the radiant energy receiving surfaces of all said cartridges facing to the same side of said array, said cartridges being supported by said supporting means in such a manner as to enable the removal and replacement of any one independently of all others, D. a rotor on said support structure and means mounting said rotor for guided rotational movement on an axis coaxially of said array, E. at least one photometer carried on said rotor, said photometer having a source of radiant energy and means forming a beam of said radiant energy and directing said beam to said cartridges, the formed beam being disposed to impinge against said cartridges at the radiant energy receiving surfaces thereof as the rotor moves relative to said circular array, F. the angle of impingement of said beam with said radiant energy receiving surfaces relative to the planes of said surfaces being such as to enable detection of reflected radiant energy, G. said photometer including photoresponsive means arranged to receive modified radiation reflected from said cartridges, the spatial relationship of the beam forming means and photoresponsive means being fixed, H. means for rotating the rotor on a program of movement to direct said beam at the cartridges selectively if not sequentially I. the photoresponsive means being responsive to the modified reflected radiation to produce an electrical signal related to the chemical condition of the sample substance, if any, carried by the cartridge which the directed beam illuminates, rotational movement of the rotor serving to produce a plurality of said signals from the sample substance of those cartridges which have been illuminated, J. said means for supporting the cartridge being arranged to tilt all of the cartridges when in position on an approximately 45° angle with the horizontal, facing the energy receiving surface of each cartridge inwardly toward said axis and downwardly, the directed beam of radiant energy being horizontal, the photoresponsive means having sensitive element means facing upward and arranged to receive the reflected energy from said cartridges as said energy passes downward, K. means for generating usable data from said signals and L. means for coupling the signals from the rotor to said last-mentioned means.

24. Apparatus for monitoring chemical reactions occurring or having occurred in a plurality of sample substances carried respectively by a plurality of cartridges of generally strip-like planar construction, the reaction occurring or having occurred in any cartridge being detected by directing a beam of radiant energy to illuminate a cartridge at a radiant energy receiving surface thereof which provides access to said substance carried by the cartridge and measuring the modified radiation reflected from the sample substance carried by said cartridge and the radiant energy receiving surface, said apparatus comprising:

A. a support structure,

B. a plurality of cartridges of generally strip-like planar construction,

C. means on said structure for fixedly supporting a plurality of said cartridges in a circular array and each cartridge having a sample substance carried thereby and a radiant energy receiving surface providing access for radiant energy to said sample substance, the radiant energy receiving surfaces of all said cartridges facing to the same side of said array, said cartridges being supported by said supporting means in such a manner as to enable the removal and replacement of any one independently of all others, D. a rotor on said support structure and means mounting said rotor for guided rotational movement on an axis coaxially of said array, E. a plurality of photometers carried on said rotor, said photometers being radially disposed on said rotor, said photometers having source means of radiant energy and each photometer having means forming a separate beam of said radiant energy and directing said beam to said cartridges, the formed beam being disposed to impinge against said cartridges at the radiant energy receiving surfaces thereof as the rotor moves relative to said circular array, F. the angle of impingement of said beam with said radiant energy receiving surfaces relative to the planes of said surfaces being such as to enable detection of reflected radiant energy, G. said photometers including photoresponsive means arranged to receive modified radiation reflected from said cartridges, the spatial relationship of the beam forming means and photoresponsive means being fixed, H. means for rotating the rotor on a program of movement to direct said beams at the cartridges selectively if not sequentially, I. the photoresponsive means being responsive to the modified reflected radiation to produce an electrical signal related to the chemical condition of the sample substance, if any, carried by the cartridge which the directed beam illuminates, rotational movement of the rotor serving to produce a plurality of said signals from the sample substances of those cartridges which have been illuminated, J. the cartridges adapted to be facing inwardly and tilted downwardly when disposed on said supporting means, said photoresponsive means comprising at least a separate photoresponsive device for each photometer arranged with a sensitive element facing upward to receive the reflected radiation from the cartridges, K. means for generating usable data from said signals and L. means for coupling the signals from the carrier to said last-mentioned means.

* * * * *

UNITED STATES PATENT AND TRADEMARK OFFICE
CERTIFICATE OF CORRECTION

PATENT NO. : 4,430,299
DATED : February 7, 1984
INVENTOR(S) : THOMAS HORNE

It is certified that error appears in the above-identified patent and that said Letters Patent are hereby corrected as shown below:

Column 5 line 50, change last occurrence of "the" to -- that --;

Column 11 line 27, change "84" to -- 184 --;

Column 13 line 51, change "10" to -- 7 --.

Signed and Sealed this

Twenty-sixth Day of June 1984

[SEAL]

Attest:

GERALD J. MOSSINGHOFF

Attesting Officer

Commissioner of Patents and Trademarks